United States Patent [19]
Luebbe et al.

[11] Patent Number: 6,013,248
[45] Date of Patent: Jan. 11, 2000

[54] DEODORANT COMPOSITIONS CONTAINING 1,2-HEXANEDIOL

[75] Inventors: John Paul Luebbe, Lawrenceburg, Ind.; Gerald John Guskey, Montgomery, Ohio; Curtis Bobby Motley, West Chester, Ohio; Thomas Vincent Orr, Cincinnati, Ohio

[73] Assignee: The Procter & Gamble Company, Cincinnati, Ohio

[21] Appl. No.: 09/071,179

[22] Filed: May 1, 1998

[51] Int. Cl.[7] ............................... A61K 7/32; A61K 7/00
[52] U.S. Cl. ............................. 424/65; 424/400; 424/401
[58] Field of Search ............................... 424/65, 400, 401

[56] References Cited

U.S. PATENT DOCUMENTS

| | | | |
|---|---|---|---|
| 4,781,917 | 11/1988 | Luebbe et al. | 424/65 |
| 4,816,261 | 3/1989 | Luebbe et al. | 424/65 |
| 5,643,558 | 7/1997 | Provancal et al. | 424/66 |

FOREIGN PATENT DOCUMENTS

| | | |
|---|---|---|
| 0 295 070 A2 | 12/1988 | European Pat. Off. . |
| 0 404 533 A1 | 12/1990 | European Pat. Off. . |
| 9-255524 | 9/1997 | Japan . |
| WO 97/31618 | 7/1997 | WIPO . |

*Primary Examiner*—Shelley A. Dodson
*Attorney, Agent, or Firm*—Joan B. Tucker; William J. Winter; Tara M. Rosnell

[57] ABSTRACT

The present invention is directed to deodorant compositions, and methods of using such compositions, wherein the compositions comprise from about 0.1% to about 99.9% by weight of a deodorant active, fragrance or combination thereof, and from about 0.1% to about 99.9% by weight of a carrier comprising 1,2-hexanediol. The deodorant composition preferably further comprises a suitable gellant or structurant to provide the desired product form, including a deodorant gel solid stick. The 1,2-hexanediol carrier is a highly effective coupling agent and is milder to the skin when applied topically to the axilla or other areas of the skin as compared to many other polyol-containing deodorant compositions. The present invention also relates to the use of triclosan/triclocarban combinations for improved deodorant efficacy.

27 Claims, No Drawings

DEODORANT COMPOSITIONS CONTAINING 1,2-HEXANEDIOL

FIELD OF INVENTION

This invention relates to deodorant compositions comprising deodorant active and a carrier comprising 1,2-hexanediol. This carrier is milder to the skin than many other polyol-containing carriers, and is especially effective as a coupling agent for gellant systems containing silicone or other carriers. The compositions provide improved clarity, and therefore include clear or translucent deodorant compositions.

BACKGROUND OF THE INVENTION

Deodorant compositions are well known for use in controlling malodors associated with human perspiration. These malodors develop from human perspiration primarily as the result of microbial interaction with sweat gland secretions which then produces pungent fatty acids. Deodorant compositions contain antimicrobial agents to help control the microbial development of such malodors, and/or they can contain deodorizing fragrances that help to mask the sensory perception of the malodors.

Deodorant compositions in gel form are especially popular as a means for preventing or masking malodor arising from perspiration. These gel deodorants compositions are typically in the form of a solid or soft solid stick and, like other deodorant products, are also applied topically to the underarm or other area of the skin. The gel deodorants typically contain a gellant or other structurant, a solvent to solubilize the gellant or other structurant, and a deodorant active such as an antimicrobial active, deodorizing fragrance or other odor masking material. These compositions may be aqueous or anhydrous systems, and typically contain a polar solvent to help solubilize the gellant or other structurant. Many of these compositions also contain diol or other polyhydric solvents such as aliphatic polyhydric alcohols having from 2 to 12 carbon atoms, common examples of which include propylene glycol, ethylene glycol, diethylene glycol, 1,2-proplyene glycol, 1,3-propylene glycol, 1,3-butylene glycol (1,3-butane-diol), glycerine (1,2,3-trihydroxy propane), 2-methyl-2,4-pentane-diol (hexylene glycol), 2-ethyl- 1,3-hexane-diol, 1,2,6-hexanetriol, and combinations thereof.

Many deodorant compositions, however, cause skin irritation when topically applied to the underarms or other sensitive areas of the skin. This irritation is attributed primarily to the diol or polyhydric solvents commonly used in such compositions. This skin irritation is especially problematic when the applied composition is an anhydrous system containing higher concentrations of the polyhydric carrier, and even more problematic in a small percentage of the population that is unusually sensitive to topical polyol irritation.

It has now been found that deodorant compositions containing 1,2-hexanediol cause less skin irritation than many other deodorant compositions containing diol or other highly polar polyol solvents. It has also been found that 1,2-hexanediol is an excellent coupling agent that not only causes less skin irritation, but can also be used at lower concentrations than many other coupling agents which further results in reduced skin irritation. The 1,2-hexanediol solvent is also very useful in formulating clear or translucent deodorant compositions.

It has also been found that deodorant compositions containing a combination of triclosan and triclocarban provides the composition with improved deodorant efficacy. This combination of actives may be used in any topical composition, including the compositions described herein.

It is therefore an object of the present invention to provide a deodorant composition and a method of using such a composition that is milder to the skin than other diol-containing deodorant compositions. It is a further object to provide such a composition that also has good skin feel characteristics during and after topical application, and/or provides improved product clarity.

SUMMARY OF THE INVENTION

The present invention is directed to deodorant compositions comprising from about 0.1% to about 99.9% by weight of deodorant active and from about 0.1% to about 99.9% by weight of a carrier comprising 1,2-hexanediol. The compositions may be aqueous or anhydrous. Preferred embodiments comprise a gellant or other suitable structurant.

The present invention is also directed to a method of controlling or inhibiting malodor associated with human perspiration, which method comprises the step of applying to the axilla area of the skin from about 0.1 gram to about 2.0 gram of the deodorant composition defined herein, wherein the deodorant composition comprises about 0.1% to about 99.9% by weight of deodorant active, deodorizing fragrance or combination thereof, and from about 0.1% to about 99.9% by weight of a carrier comprising 1,2-hexanediol, or wherein the deodorant composition comprises a combination of triclocarban and triclosan.

It has now been found that the selection of 1,2-hexanediol as a solvent or coupling agent in an deodorant composition provides the composition with improved performance relative to other polyol-containing deodorant compositions. In particular, 1,2-hexanediol has been found to be milder to the skin than many other similar polyol-containing solvents, and is more effective as a coupling agent than many other commonly used diol solvents, and/or provides improved product clarity. These compositions also provide improved skin feel performance, aesthetics, and/or product stability as compared to many other polyol-containing deodorant compositions.

It has also been found that the combination of triclosan and triclocarban when applied topically to the axilla or other area of the skin provides improved deodorant efficacy that is greater than the additive deodorant benefits that would otherwise be expected from such a combination. The triclosan/triclocarban combination is effective in providing for improved deodorant performance from the deodorant composition of the present invention, or when applied from any other topical deodorant composition that contains this active combination and that is otherwise suitable for application to human skin.

DETAILED DESCRIPTION

The deodorant compositions of the present invention include deodorant compositions in final or intermediate product form, and include product forms such as solid or gel sticks, soft solids or creams, lotions or other liquids, aerosol or pump sprays, and so forth. These deodorant compositions are intended for topical application to the underarm or other suitable areas of the skin, or are intended for use as formulation intermediates in the manufacturing process of other final deodorant product forms.

The term "ambient conditions" as used herein refers to surrounding conditions at about one atmosphere of pressure, 50% relative humidity, and about 25° C.

The solubility parameters for various solvents or other materials described herein are determined by methods well known in the chemical arts for establishing the relative polar character of a solvent or other such material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

The term "volatile" as used herein refers to those materials which have a measurable vapor pressure as measured at 25° C. Such vapor pressures will typically range from about 0.01 mmHg to about 6 mmHg, more typically from about 0.02 mmHg to about 1.5 mmHg, and have an average boiling point at about 1 atm which is typically less than about 250° C., more typically less than about 235° C., at 1 atmosphere (atm) of pressure.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The deodorant compositions and methods of the present invention can comprise, consist of, or consist essentially of the essential elements and limitations of the invention described herein, as well as any of the additional or optional ingredients, components, or limitations described herein.

Deodorant Active and Fragrance

The deodorant compositions of the present invention comprise a deodorant active, fragrance or combination thereof at concentrations ranging from about 0.001% to about 50%, preferably from about 0.01% to about 20%, more preferably from about 0.1% to about 10%, even more preferably from about 0.1% to about 5%, by weight of the composition. These deodorant actives and fragrance include any known or otherwise safe and effective deodorant active or fragrance suitable for topical application to human skin.

Unless otherwise specified, the term "active" as used herein refers generally to deodorant actives or fragrances, whereas the term "deodorant active" specifically refers to topical materials which can prevent or eliminate malodors resulting from perspiration. The term "fragrance" as used herein specifically refers to any topical material which covers or masks malodors resulting from perspiration, or which otherwise provides the composition with the desired perfumed aroma.

A) Deodorant active

Deodorant actives suitable for use in the deodorant composition of the present invention includes any topical material that is known for or is otherwise effective in preventing or eliminating malodor associated with perspiration. These deodorant actives are typically antimicrobial agents (e.g., bacteriocides, fungicides), malodor-absorbing material, or combinations thereof.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Preferred deodorant actives are triclosan, triclocarban and combinations thereof, wherein the preferred concentration of either triclosan or triclocarban ranges from about 0.01% to about 1.0%, more preferably from about 0.1% to about 0.5%, even more preferably from about 0.1% to 0.3%, by weight of the composition, and wherein the total concentration of triclosan and triclocarban when used together in a composition ranges from about 0.01% to about 2.0%, more preferably from about 0.2% to about 1.0%, even more preferably from about 0.2% to about 0.6%, by weight of the composition. It has been found that the combination of these two deodorant actives provides a deodorant efficacy that exceeds the cumulative deodorant efficacy that one would otherwise predict from such a combination.

The preferred combination of triclosan and triclocarban is effective in providing improved deodorant performance from the deodorant compositions described herein, or from any deodorant or topical composition containing such a combination that is otherwise suitable for application to human skin. The present invention is therefore also directed to a method of controlling malodor associated with human perspiration by topically applying the triclosan/triclocarban combination described above, or any other suitable composition containing the triclosan/triclocarban combination described above, to the underarm or other area of the skin. From most deodorant compositions containing this combination, from about 0.1 gram to about 2.0 gram per axilla of the deodorant composition is applied, preferably once or twice daily, more preferably once daily.

Other deodorant actives include odor-absorbing materials such as carbonate and bicarbonate salts, including alkali metal carbonates and bicarbonates, ammonium and tetraalkylammonium Preferred are sodium and potassium salts of such odor-absorbing materials.

Other deodorant actives include antiperspirant actives such as astringent astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof. Non limiting examples of suitable antiperspirant actives for use herein are described in U.S. Pat. No. 5,429,816, which description is incorporated herein by reference.

B) Fragrance

Fragrances suitable for use in the deodorant composition of the present invention include any topical material that is known for or is otherwise effective in masking malodor associated with perspiration, or which otherwise provides the composition with the desired perfumed aroma. These fragrances include any perfume or perfume chemical suitable for topical application to the skin.

The concentration of the fragrance in the deodorant composition should be effective to provide the desired aroma characteristics or to mask malodor, wherein the malodor is inherently associated with the composition itself or is associated with malodor development from human perspiration. Also, the fragrance and whatever carriers accompany it should not impart excessive stinging to the skin, especially broken or irritated skin, at the levels previously disclosed. The fragrance will typically be in the form of water insoluble perfumes that are solubilized in the deodorant composition herein.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-anolide-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable fragrances are those which mask or help to mask odors associated with perspiration (hereinafter referred to as odor masking fragrances), some non-limiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The fragrance for use herein may also contain solubilizers, diluents, or solvents which are well known in the art. Such materials are described in Arctander, Perfume and Flavour Chemicals (Aroma Chemicals), Vol. I and II (1969). These materials typically include small amounts of dipropylene glycol, diethylene glycol, $C_1$–$C_6$ alcohols, and/or benzyl alcohol.

Liquid Carrier

The deodorant composition of the present invention comprises from about 0.1% to about 99.9% by weight of a liquid carrier comprising 1,2-hexanediol, preferably a liquid carrier comprising a combination of 1,2-hexanediol and one or more other known or otherwise effective liquid carrier materials. The carrier is a liquid under ambient conditions, and therefore includes carrier liquid combinations or combinations of carrier liquids and dissolved carrier solids, provided that any such combination is in liquid form under ambient conditions.

The deodorant compositions of the present invention may be formulated as an aqueous or anhydrous composition. For an aqueous formulation, the deodorant compositions may further comprise from about 10% to about 75% by weight of water, preferably from about 10% to about 60% by weight of water, even more preferably from about 15% to about 50%, by weight of water. For an anhydrous formulation, deodorant compositions contain less than about 10%, more preferably less than about 3%, even more preferably less than about 1%, even more preferably zero percent, by weight of water.

The concentration of 1,2-hexanediol in the deodorant composition of the present invention ranges from about 0.1% to about 99.9% by weight of the deodorant composition, but specific 1,2-hexanediol concentrations may vary greatly depending upon variables such as 1) the function to be served by the 1,2-hexanediol, 2) the desired product form, viscosity, and hardness of the deodorant composition, 3) whether the deodorant composition is in final or intermediate form, and 4) other formulation variables well know in the chemical or formulation arts. For most product forms, the concentration of 1,2-hexanediol in the deodorant composition ranges from about 0.1% to about 70%, more preferably from about 1% to about 40%, even more preferably from about 5% to about 25%, by weight of the deodorant composition.

In addition to the 1,2-hexanediol carrier, the deodorant composition may further comprise one or more optional liquid carriers suitable for topical application and appropriate for the product form desired. Such other optional carriers include any known or otherwise effective liquid carrier material for use in deodorants or other topical compositions. In the event that the optional liquid carrier is not readily miscible or dispersible in 1,2-hexanediol or other materials in the liquid carrier component, then other liquid carriers or coupling agents may be added to the composition to bring the 1,2-hexanediol and other immiscible or nondispersible materials (e.g., nonpolar solvents) into a homogenous solution or dispersion.

The concentration of all carrier liquids in the deodorant composition for most product forms, including deodorant gels or gel solid sticks, typically ranges from about 10% to about 90%, preferably from about 30% to about 70%, by weight of the deodorant composition. In this context, the term "all carrier liquids" refers to the combination of 1,2-hexanediol and optional carrier liquids, including water if present.

Optional liquid carriers for use in combination with 1,2-hexanediol in the deodorant composition include any topically safe and effective organic, silicone-containing or fluorine-containing, volatile or non-volatile, polar or non-polar carrier liquid, provided that the resulting combination of carrier materials forms a solution or other homogenous liquid or liquid dispersion at the selected processing temperature of the composition. Processing temperatures for the deodorant compositions typically range from about 28° C. to about 250° C., more typically from about 28° C. to about 110° C., and even more typically from about 28° C. to about 100° C.

Optional liquid carriers include moderately ethoxylated ethers of fatty alcohols having from about 8 to about 30 carbon atoms, esters of polyhydric alcohols, esters of fatty acids, polyethylene glycols having at least 8 ethoxylate groups, polypropylene glycols having at least 8 propoxylate groups, and combinations thereof. Specific non-limiting of such solvents include propyleneglycol monoisostearate; PPG-3 myristyl ether; PEG-8; 1,2, pentanediol, PPG-14 butylether, dimethyl isosorbide, and combinations thereof.

Optional liquid carriers include C1 to C20 monohydric alcohols, preferably C2 to C8 monohydric alcohols; C2 to C40 dihydric or polyhydric alcohols other than 1,2-hexanediol, preferably C2 to C20 dihydric or polyhydric alcohols; alkyl ethers of all such alcohols (preferably C1–C4 alkyl ethers); and polyalkoxylated glycols such as propylene glycols and polyethylene glycols having from 2 to 7 repeating alkoxylate (e.g., ethoxylate or propoxylate) groups; polyglycerols having from 2 to 16 repeating glycerol moieties; derivatives and combinations thereof.

Specific examples of such optional liquid carriers include propylene glycol, hexylene glyol, dipropylene glycol, tripropylene glycol, glycerin, ethanol, propylene glycol methyl ether, dipropylene glycol methyl ether, dipropylene glycol, tripropylene glycol, ethanol, n-propanol, n-butanol, t-butanol, 2-methoxyethanol, 2-ethoxyethanol, ethylene glycol, isopropanol, isbutanol, 1,4-butylene glycol, 2,3-butylene glycol, 2,4-dihydroxy-2-methylpentane, trimethylene glycol, 1,3-butanediol, 1,4,-butanediol, and combinations thereof. Other similar but suitable solvents for use as optional liquid carriers are described, for example, in U.S. Pat. No. 4,781,917 (Luebbe et al.), U.S. Pat. No. 5,643,558 (Provancal et al.), U.S. Pat. No. 4,816,261 (Luebbe et al.), EP 404 533 A1 (Smith et al.), which descriptions are incorporated herein by reference.

Other optional liquid carriers include benzoate co-solvents, cinnamate esters, secondary alcohols, benzyl acetate, phenyl alkane and combinations thereof.

Preferred optional liquid carriers include PPG-3-myristyl ether, diisopropyl adipate, PPG-14 butyl ether, dimethicone copolyols, and combinations thereof.

Other optional liquid carriers include modified or organofunctional silicone carriers such as polyalkylsiloxanes, polyalkyarylsiloxanes, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Suitable modified silicone carriers include, but are not limited to, compounds or materials such as those defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the deodorant compositions herein include the following modified silicones available from Dow Corning: DC-556 Cosmetic Grade Fluid (phenyl trimethicone); DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-1401 (Cyclomethicone [and] Dimethiconol); DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-1-3563 (Dimethiconal); DC-X2-1286 (Dimethiconol); DC-X2-1146A (Cylcomethicone [and] Dimethiconol); DC-7224 (Trimethylsilylamodimethicone); DC-X2-1318 Fluid (Cyclomethicone [and] Vinyldimethicone); DC-QF1-3593A fluid (Triinethylsiloxysilicate) and combinations thereof.

Other nonlimiting examples of suitable modified silicone carriers for use in the deodorant compositions herein include the following modified silicones available from General Electric: GE CF-1142 (Methylphenyl Siloxane Fluid); GE SF-1328; GE SF-1188 (Dimethicone copolyol); GE SF-1188A and combinations thereof.

Other nonlimiting examples of suitable modified silicone carriers for use in the deodorant compositions herein include the following modified silicones available from Goldschmidt: Abil EM-90 (silicone emulsifier); Abil EM-97 (polyether siloxane); Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers) and combinations thereof.

Other nonlimiting examples of suitable modified silicone carriers for use in the deodorant compositions herein include the following: Masil 756 from PPG Industries (Tetrabutoxypropyl Trisiloxane); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The deodorant composition of the present invention preferably comprises a volatile silicone carrier in combination with 1,2 hexanediol. The concentration of the volatile silicone preferably range from about 10% to about 90%, more preferably from about 15% to about 65%, by weight of the deodorant composition. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

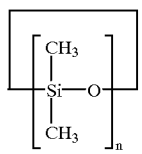

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

Optional liquid carriers may also include a non-volatile silicone carrier other than or in addition to the preferred modified silicone carriers described hereinbefore. These non-volatile silicone carriers are preferably linear silicones which include, but are not limited to, those which conform to either of the formulas:

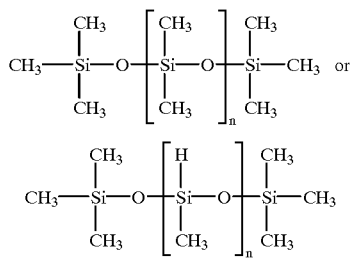

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the deodorant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF- 1066 and SF 18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The deodorant composition preferably comprises a combination of volatile and nonvolatile silicone materials, more preferably a combination of volatile and nonvolatile silicone carrier liquids. Nonlimiting examples of suitable combinations of such silicone materials are described in U.S. Pat. No. 5,156,834 (Beckmeyer et al.), which descriptions are incorporated herein by reference.

Other optional liquid carriers include volatile and nonvolatile, non-polar, carriers such as mineral oil, petrolatum, isohexadecane, isododecane, various other hydrocarbon oils, and combinations thereof. In this context, the term "nonpolar" refers to those solvents having a solubility parameter of less than 8.0 $(cal/cm^3)^{0.5}$, preferably from about 5.0 $(cal/cm^3)^{0.5}$ to less than 8.0 $(cal/cm^3)^{0.5}$, more preferably from 6.0 $(cal/cm^3)^{0.5}$ to about 7.60 $(cal/cm^3)^{0.5}$.

Suitable volatile nonpolar solvents are those solvents having the above-described vapor pressure and solubility parameters, which can also include hydrocarbons, esters, amides, and ethers having the requisite vapor pressure and solubility parameter, Preferred are nonpolar hydrocarbon solvents which can be cyclic, branched or chain configurations, most preferably branched chain hydrocarbons.

Preferred volatile nonpolar solvents are the branched chain hydrocarbons having the requisite vapor pressure and solubility parameter and having from about 4 to about 30 carbon atoms, preferably from about 4 to about 20 carbon atoms, more preferably from about 6 to about 20 carbon atoms. Specific non-limiting examples of these nonpolar volatile solvents include the isoparaffins available from Exxon Chemical Company, Baytown, Tex. U.S.A, as Isopar M (C13-C14 isoparaffin), Isopar C (C7-C8 Isoparaffin), C8-C9 Isoparaffin (Isopar E), Isopar G (C10-11 Isoparaffin), Isopar L (C11-C13 Isoparaffin) and Isopar H (C11-C12 Isoparaffin). Other nonlimiting examples of suitable branched chain hydrocarbons include Permethyl 99A (isododecane), Permethyl 102A (isoeicosane), Permethyl 101A (isohexadecane), and combinations thereof. The Permethyl series are available from Preperse, Inc., South Plainfield, N.J. U.S.A. Other non-limiting examples of suitable branched chain hydrocarbons include petroleum distallates such as those available from Phillips Chemical as Soltrol 130, Soltrol 170, and those available from Shell as Shell Sol 70, -71, and -2033, and combinations thereof.

Nonlimiting examples of other suitable nonpolar volatile solvents include dibutyl adipate, diisopropyladipate, dodecane, octane, decane and combinations thereof, and the Norpar series of paraffins available from Exxon Chemical Company as Norpar 12, -13, and -15. Yet another example includes C11-C15 alkanes/cycloalkanes available from Exxon as Exxsol D80.

Other optional liquid carriers for use in combination with the 1,2-hexanediol includes fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the series fluorosurfactants from Dupont Performance Chemicals under the trade name Zonyl® Fluorosurfactants.

Gellant

The deodorant composition of the present invention are preferably in the form of gel solid deodorants, and which preferably comprises a gellant or other structurant suitable for providing the desired hardness and application characteristics to the composition. The gellant or structurant concentrations preferably range from about 0.01% to about 20%, preferably from about 0.1% to about 10%, more preferably from about 1% to about 8%, even more preferably from about 3% to about 7%, by weight of the deodorant composition.

Any known gellant or structurant may be used in the gel deodorant composition of the present invention provided that the selected gellant or structurant can melt and form a solution or other homogenous liquid or liquid dispersion with the liquid carrier as defined herein at a processing temperature of from about 50° C. to about 150° C., preferably from about 50° C. to about 120° C., more preferably from about 60° C. to about 100° C. The selected gellant or structurant must also provide the deodorant composition with the desired gel matrix and product hardness after formulation and completion of processing.

Preferred gellants or structurants are salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate.

Non-limiting examples of fatty acids suitable for making the fatty acid gellants or structurants include acids such as myristic, palmitic, stearic, oleic, linoleic, linolenic, margaric and combinations thereof. These fatty acids are preferably derived from sources such as coconut oil, beef tallow, lanolin, fish oil, beeswax, palm oil, peanut oil, olive oil, cottonseed oil, soybean oil, corn oil, rapeseed oil, rosin acids, greases, and other natural sources, or are derived by synthetic or semisynthetic methods well known to those skilled in the formulation art.

Other suitable gellants or structurants include hydroxy acids, fatty acids, esters and amides of fatty acids and fatty acid salts, hydroxy fatty acids, cholesterolic materials, lanolinolic materials, and other amide gellants known for use as gelling agents or which are otherwise described in detail hereinafter.

Nonlimiting examples of suitable fatty acid gellants or structurants include fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, combinations thereof, and salts thereof.

Other nonlimiting examples of specific gellants or structurants suitable for use in the deodorant composition include those which correspond to the following formula:

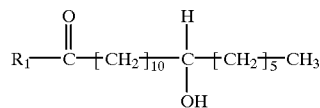

wherein $R_1$ is $OR_2$ or $NR_2R_3$ or silicone containing; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

Nonlimiting examples of suitable amide gellants or structurants for use in the deodorant composition include disubstituted or branched monoamide gellants, monosubstituted or branched diamide gellants, triamide gellants, and combinations thereof. Preferred are alkyl amides of di- and/or tri-basic carboxylic acids or anhydrides which conform to the formula:

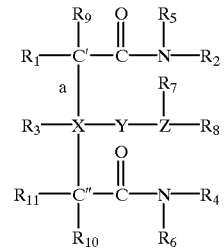

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nil, nitrogen, aryl or $-(CH_2)_n$ where n is an integer from 1 to 6, preferably $-(CH_2)_n$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
 (i) when X is nil, Y, Z, $R_3$, $R_7$ and $R_8$ are nil, C' is bonded directly to C''' and $R_1$ is not a hydrogen;
 (ii) when X and Z are not nil and Y is nil, X is directly bonded to Z;
 (iii) when Z is nil, a hydrogen or a hydroxy, $R_7$ and $R_8$ are nil; and
 (iv) when "a" is a double bond, $R_3$ and $R_8$ are nil.

Nonlimiting examples of specific alkyl amide gellants suitable for use in the deodorant composition include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-trioctylamide, N,N',N''-tri(acetodecylamide)amine, 2-dodecyl-N,N'-dihexylsuccinamide, and 2 dodecyl-N,N'-dibutylsuccinamide.

Optional Ingredients

The deodorant compositions of the present invention may further comprise one or more optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants, antiperspirants or other personal care compositions, and may also be used in the deodorant compositions herein, provided that such optional materials are compatible with the essential materials described herein, or do not otherwise unduly impair product performance.

Nonlimiting examples of optional ingredients suitable for use in the deodorant compositions herein include pH buffering agents; additional emollients; humectants; soothing agents; dyes and pigments; medicaments; baking soda and related materials, preservatives; and soothing agents such as aloe vera, allantoin, D-panthenol, avocado oil and other vegetative oils, and lichen extract.

Skin Irritation

It has been found that the deodorant compositions of the present invention, which contain 1,2-hexanediol, are less irritating to the skin than other similar compositions containing liquid polyols such as propylene glycol. To emphasize this benefit, the compositions described in Table 1 are evaluated for skin irritation in a three day patch test. Skin irritation potential is measured by visual grading of skin erythema (redness) by qualified skin graders using a 0 (no apparent skin irritation) to 4 (severe skin irritation) grading scale. Data are reported as a least square mean average (LS mean score) of 22 panelists with statistics.

TABLE 1

| Composition | LS mean score | Statistical grouping |
|---|---|---|
| A 25% active + HD | 0.182 | a |
| B 25% active + PG | 0.591 | b |

The data set forth in Table 1 shows that compositions containing deodorant/antiperspirant active solubilized in 1,2-hexanediol is less irritating (statistically significant at 95% confidence) to the skin than compositions containing antiperspirant/deodorant active solubilized in propylene glycol.

Method of Manufacture

The compositions of the present invention may be made by any of the methods known in the art for formulating deodorant compositions, or which are otherwise effective in formulating such compositions. As will be apparent to those skilled in the art, the particular method will be dependent upon the selection of the specific types and amounts of the components employed, as well as the final product form desired, e.g., liquid, solid sticks, soft solids, creams, lotions, single or multiple phase systems containing solid or dissolved active, suspensions or solutions, clear or translucent or opaque, etc.

In general, the deodorant compositions of the present invention can be prepared by merely combining the liquid carrier with the deodorant active. Optional gellants or structurants may then be added with agitation and heat to a temperature of from about 75° C. to about 100° C. to allow the gellant or structurant to melt and form a substantially clear or translucent liquid. The resulting solution is cooled before adding fragrance (if applicable), and then the cooled composition is poured into an appropriate container or dispenser at about 70° C. and allowed to solidify within the container or dispenser by cooling or allowing to cool the contained composition to ambient temperature.

Method For Use

The deodorant composition of the present invention may be used as an intermediate in formulating other deodorant compositions, or it may be formulated in final form to be topically applied to the axilla or other area of the skin in any known or otherwise effective method for controlling malodor associated with perspiration. These methods comprise applying to the axilla or other area of the human skin a safe and effective amount of the deodorant composition of the present invention. In this context, the term "safe and effective amount" means an amount of the deodorant composition topically applied to the skin which is effective in inhibiting or minimizing or masking perspiration malodor at the site of application while also being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or more times daily, preferably once daily.

EXAMPLES

The following Examples 1–8 illustrate specific embodiments of the deodorant compositions of the present invention, including methods of manufacture and use, but are not intended to be limiting thereof. Other modifications can be undertaken by the skilled artisan without departing from the spirit and scope of this invention.

Each of the exemplified compositions is applied topically to the underarm in an amount effective to inhibit, prevent or mask perspiration malodor in humans, typically an amount which ranging from about 0.1 gram to about 2 grams per axilla. The applied compositions are effective in inhibiting the development of malodors or in masking the sensory perception of such malodors resulting from perspiration from the applied areas, and have good skin feel characteristics during and after application. The applied compositions are milder to the skin and cause little or no skin irritation. All exemplified amounts are weight-weight percents based on the total weight of the composition, unless otherwise specified.

The compositions described in Table 2 are aqueous gel deodorant sticks, whereas the compositions described in Table 3 are anhydrous gel deodorant sticks.

Examples 1–3

Each of the compositions described in Table 2 are in the form of clear or translucent aqueous gel deodorant sticks that can be formulated by conventional formulation methods described herein.

TABLE 2

| | Examples | | |
|---|---|---|---|
| Ingredient | 1 | 2 | 3 |
| Triclosan | 0.30 | 0.50 | 0.30 |
| Triclocarban | 0.30 | 0.25 | 0.50 |
| 1,2-hexanediol | 20.00 | 50.00 | 20.00 |
| Dipropylene glycol | 30.00 | — | — |
| Propylene glycol | 16.00 | 20.00 | 50.00 |
| Sodium stearate | 6.00 | 6.00 | 5.00 |
| Water | 24.70 | 20.75 | 22.50 |
| Perfume | 2.70 | 2.50 | 1.70 |

Examples 4–8

Each of the compositions described below are in the form of clear or translucent anhydrous gel deodorant sticks that can be formulated by conventional formulation methods described herein.

TABLE 3

| | Examples | | | | |
|---|---|---|---|---|---|
| Ingredient | 4 | 5 | 6 | 7 | 8 |
| Triclosan | — | — | 0.50 | — | — |
| 1,2-hexanediol | 25.00 | 20.13 | 18.10 | 24.20 | 20.95 |
| Hexylene glycol | — | — | — | 24.20 | 20.95 |
| PPG-3 Myristyl ether | 26.00 | 20.13 | 22.70 | 3.50 | 3.50 |
| Isopar M | 18.00 | 18.00 | 18.00 | 18.00 | 20.55 |
| Isopar L | 18.00 | 18.00 | 18.00 | 20.55 | 18.00 |
| Sodium stearate | 13.00 | 8.50 | 6.20 | 6.55 | 6.55 |
| Propylene glycol monoisostearate | — | 6.50 | 6.50 | — | 6.50 |
| Glycerin | — | 5.20 | 5.00 | — | — |
| Perfume | — | 3.54 | 3.50 | 3.00 | 3.00 |
| Dye | — | — | 1.5 | — | — |

What is claimed is:

1. A deodorant composition comprising:
   A) from about 0.1% to about 99.9% by weight of 1,2-hexanediol; and
   B) from about 0.1% to about 99.9% by weight of deodorant active.

2. The deodorant composition of claim 1 wherein the composition comprises from about 1% to about 70% by weight of 1,2-hexanediol.

3. The deodorant composition of claim 2 wherein the composition comprises from about 5% to about 25% by weight of 1,2-hexanediol.

4. The deodorant composition of claim 2 wherein the composition further comprises from about 0.01% to about 20% by weight of a gellant.

5. The deodorant composition of claim 4 wherein the gellant is a fatty acid salt having from about 12 to about 40 carbon atoms.

6. The deodorant composition of claim 5 wherein the fatty acid salt is a metal salt of stearic acid.

7. The deodorant composition of claim 1 wherein the deodorant active is selected from the group consisting triclosan, triclocarban, and combinations thereof.

8. The deodorant composition of claim 7 wherein the deodorant active is selected from the group consisting of from about 0.01% to about 1.0% by weight of triclosan, from about 0.01% to about 1.0% by weight of triclocarban, and combinations thereof.

9. The deodorant composition of claim 8 wherein the deodorant active is a combination of from about 0.01% to about 1.0% by weight of triclosan and from about 0.01% to about 1.0% by weight of triclocarban.

10. The deodorant composition of claim 9 wherein the composition is an anhydrous system comprising less than 3% by weight of water.

11. The deodorant composition of claim 10 wherein the composition contains less than 1% by weight of water.

12. The deodorant composition of claim 4 wherein the composition further comprises from about 0.01% to about 15% by weight of a solvent in addition to the 1,2-hexanediol, wherein the additional solvent is selected from the group consisting of C1 to C20 monohydric alcohols, polypropylene glycols having from 2 to 7 repeating propoxylate groups, polyethylene glycols having from 2 to 7 repeating ethoxylate groups, polyglycerols having from 2 to 16 repeating glycerol groups, and combinations thereof.

13. A method for controlling malodor associated with human perspiration, which method comprises the step of applying to an underarm area of the skin from about 0.1 gram to about 2.0 grams of a deodorant composition comprising A) from about 0.1% to about 99.9% by weight of 1,2-hexanediol; and B) from about 0.1% to about 99.9% by weight of deodorant active, fragrance or combination thereof.

14. The method of claim 13 wherein the deodorant composition comprises from about 1% to about 40% by weight of 1,2-hexanediol.

15. The method of claim 14 wherein the deodorant composition comprises from about 5% to about 25% by weight of 1,2-hexanediol.

16. The method of claim 14 wherein the deodorant composition further comprises from about 0.01% to about 20% by weight of a gellant.

17. The method of claim 16 wherein the gellant is a fatty acid salt having from about 12 to about 40 carbon atoms.

18. The method of claim 17 wherein the fatty acid salt is a metal salt of stearic acid.

19. The deodorant composition of claim 14 wherein the deodorant active is selected from the group consisting triclosan, triclocarban, and combinations thereof.

20. The deodorant composition of claim 19 wherein the deodorant active is selected from the group consisting of from about 0.01% to about 1.0% by weight of triclosan, from about 0.01% to about 1.0% by weight of triclocarban, and combinations thereof.

21. The deodorant composition of claim 20 wherein the deodorant active is a combination of from about 0.01% to about 1.0% by weight of triclosan and from about 0.01% to about 1.0% by weight of triclocarban.

22. The method of claim 14 wherein the composition is an anhydrous gel deodorant comprising less than about 3% by weight of water.

23. The method of claim 14 wherein the composition further comprises from about 0.01% to about 15% by weight of a solvent in addition to the 1,2-hexanediol, wherein the additional solvent is selected from the group consisting of C1 to C20 monohydric alcohols, polypropylene glycols having from 2 to 7 repeating propoxylate groups, polyethylene glycols having from 2 to 7 repeating ethoxylate groups, polyglycerols having from 2 to 16 repeating glyerol groups, and combinations thereof.

24. A method for controlling malodor associated with perspiration by applying to the underarm or other area of the skin a deodorant composition comprising:

(A) from about 0.01% to about 1.0% by weight of triclosan, and (B) from about 0.01% to about 1.0% by weight of triclocarban.

25. The method of claim 24 wherein the composition comprises from about 0.1% to about 0.5% by weight of triclosan and from about 0.1% to about 0.5% by weight of triclocarban.

26. The method of claim 24 wherein the deodorant composition further comprises from about 1% to about 40% by weight of 1,2-hexanediol.

27. The method of claim 26 wherein the deodorant composition further comprises from about 0.01% to about 20% by weight of a gellant.

* * * * *